United States Patent [19]

Perovitch et al.

[11] Patent Number: 5,629,022
[45] Date of Patent: May 13, 1997

[54] METHOD FOR GALENICALLY PREPARING A THERAPEUTIC COMPOSITION BASED ON ASPIRIN

[76] Inventors: Philippe Perovitch, 251 Avenue de la Marne, 33700 Merignac; Marc Maury, 17, rue des Augustins, 33000 Bordeaux, both of France

[21] Appl. No.: 465,372

[22] Filed: Jun. 5, 1995

Related U.S. Application Data

[63] Continuation of Ser. No. 856,976, filed as PCT/FR91/00619 Jul. 25, 1991 published as WO92/01444 Feb. 6, 1992, abandoned.

[30] Foreign Application Priority Data

Jul. 26, 1990 [EP] European Pat. Off. ............... 90402150

[51] Int. Cl.$^6$ ...................................................... A61K 9/14
[52] U.S. Cl. ........................ 424/489; 424/439; 424/458
[58] Field of Search ................................ 424/489, 490, 424/439, 458

[56] References Cited

U.S. PATENT DOCUMENTS

| | | | |
|---|---|---|---|
| 4,206,209 | 6/1980 | Kracauer | 424/234 |
| 4,985,252 | 1/1991 | Jung et al. | 424/439 |
| 5,043,167 | 8/1991 | Rotini et al. | 424/489 |
| 5,139,774 | 8/1992 | Meinard et al. | 424/489 |

FOREIGN PATENT DOCUMENTS

| | | |
|---|---|---|
| 1349158 | 3/1974 | United Kingdom . |
| 1468557 | 3/1977 | United Kingdom . |
| 2188843 | 4/1987 | United Kingdom . |

*Primary Examiner*—Thurman K. Page
*Assistant Examiner*—William E. Benston
*Attorney, Agent, or Firm*—Fisher, Christen & Sabol

[57] ABSTRACT

Preparation method for preparing a therapeutical composition for internal use, particularly to be administered by mouth, in galenical presentation, and containing at least one active principle in solid form adsorbed on a substrate, the active product being distributed therein as finely dispersed microparticles. The method includes dissolving the starting active principle in an appropriate solvent, impregnating the solution thus formed on a food support having an appropriate structure and pharmaceutically compatible with the active principle, and evaporating the solvent from the solution adsorbed in the support by causing the reconstitution of the active principle by formation of microcrystals adsorbed on the walls of the substrate and within the substrate. The solvent is comprised of a binary system including a main solvent of organic nature and an adjuvent of the solid type at room temperature and soluble in the main solvent. The adjuvent additionally has lubricating properties.

10 Claims, 1 Drawing Sheet

METHOD FOR GALENICALLY PREPARING A THERAPEUTIC COMPOSITION BASED ON ASPIRIN

This application is a continuation of prior U.S. application Ser. No. 07/856,976, filed as PCT/FR91/00619 Jul. 25, 1991 published as WO92/01444 Feb. 6, 1992, now abandoned.

The invention relates to the galenic presentation of a therapeutical composition.

It has been sought to obtain active products in the microdispersed state, distributed within a substrate itself of receiving structure by proceeding with the dissolution of the active principle (insoluble or very sparingly soluble in water) in an organic solvent, after which the substrate thus impregnated with the solution is then subjected to a phase of evaporation of the solvent, the active product thus being forced to recrystallize within the support structure in the form of crystals of small dimensions and consequently presenting the desired high specific surface.

A method of this type is described in particular in European Patent Application 0287488 but, despite the theoretical interest of this method, it has appeared that execution thereof encountered practical difficulties at the level of the exploitation of manufacture, in an industrial context.

The principal difficulty, resulted from the lack of homogeneity between the substrate and the particles constituting the microcrystals adsorbed within and on the surface of the substrate, particularly on the rough surface of the latter.

By the lack of a homogeneous bond between the two solids, their cohesion cannot be ensured during the phases that the substrate and its content must successively undergo to be taken to the acceptable definitive galenic form, that of a tablet.

In fact, it is ascertained that, during the phase of evaporation in vacuo, for example, the force of suction which it is necessary to employ to ensure a profitable treatment and rapid evacuation of the solvent leads to separation of the assembly, the microcrystals constituted, as desired, by a minute dust, of the order of some microns, are entrained to some extent eluted by the gaseous current which sucks them and which consequently impoverishes the substrate, furthermore causing a notable loss of active products.

This phenomenon is found again during the subsequent phases of treatment, the difference in size between the substrate and the microcrystals causes difficult problems when forming tablets. The presence of the microcrystals constitutes an excess of forces of friction and of adherence and in fact limits the flow properties of the mixture in the presses and the operation of high-speed and high-yield production machines is more than compromised.

Finally, the high specific surface of the microcrystals which is desirable within the framework of the purpose aimed at by the invention, increases the phenomena of seizure encountered during manufacture of the tablets, the lubricants conventionally used for manufacturing the tablets not being sufficiently efficient to ensure maintenance of the desirable conditions of rates and quality, in particular when the phenomena of seizure which become too great, cause defects in quality in the tablets. Consequently, the implementation of a technique of microdispersion at high concentration on a substrate has not been able to be obtained in practice on an industrial scale despite the interest that it would represent from the galenic and commercial standpoints.

The invention makes it possible to overcome this drawback and it provides conditions which ensure homogeneity of the substrate and of the microcrystals adsorbed on the support, allowing the latter to be treated by conventional manufacturing machines thus avoiding the drawbacks which were set forth hereinabove.

To that end, the invention envisages an embodiment for carrying out the method for making microdispersions which ensures in the first place a homogeneity in the distribution of the microcrytals within a substrate which has become porous and spongy during the operations, starting from a cross-linked state, and guarantees the stability of these microcrystals once placed in position, preventing any loss or separation during manufacture.

The invention concerns more particularly a method for preparing a therapeutical composition for internal use, particularly to be administered by mouth, in galenical presentation and containing at least one active principle in solid form adsorbed on a substrate, the active product being distributed therein in the state of finely dispersed microparticles and the method being of the type comprising the phases:

- of dissolution of the starting active principle(s) in an appropriate solvent,
- of impregnation of the solution thus formed on a food support of appropriate structure and pharmaceutically compatible with said active principle,
- of evaporation of the solvent from the solution adsorbed within said support, causing reconstitution of the active principle by the formation of microcrystals adsorbed on the walls and within the substrate.
- and the method is characterized in that the solvent is constituted by a binary system comprising a main solvent, of organic nature, and an adjuvant of solid type at ambient temperature and soluble in the main solvent, the adjuvant additionally presenting lubricating properties.

Thanks to the implementation of the invention, during formation of the microcrystals, on the one hand, a limitation of their crystalline spread is obtained and, on the other hand, the maintenance in place and the firm bond of these microcystals on the wall of the substrate thanks to the presence of said adjuvant which ensures a cimentation of the microcrystals on their adsorption wall avoiding any parasitic entrainment and any subsequent dispersion during the subsequent phases of manufacture; but also, a regularization of the granulated general external form of the substrate is obtained, which facilitates industrial use thereof.

More particularly, the method of the invention is characterized in that the substrate, after absorption of the solution, is subjected to an operation of evacuation of the solvent at ambient temperature by reduction of the atmospheric pressure, i.e. by drying in vacuo; consequently, the substrate acquires by this application a regular, porous, spongy structure which conceals the microcrystals of active principle.

According to a particular feature, the formation phase comprises the homogenization of the substrate followed by a compression with a view to forming unitary doses and constituting pastilles, tablets, pellets or pills.

And it will be understood that, during the manufacture thus carried out, the adjuvant, thanks to its particular properties, attenuates the forces of friction issuing from the surfaces in contact and will make it possible to contribute within the very mass of the substrate, as on the outer walls of the tablet being formed, the properties of slide of the elements and walls on one another adapted to ensure the final texturation.

The invention is more particularly applicable to the presentation of an antalgic or anti-inflammatory speciality based on aspirin for local use or with direct assimilation via the sublingual mucouses, for general therapeutic specialities advantageously taken by the sublingual route.

According to another characteristic, the binary solvent used comprises by way of main solvent an alcohol with low vapour pressure and more especially a lower monofunctional alcohol selected from the family comprising methanol, ethanol, butanol and propanol.

More especially, an alcohol is used, presenting at the start a concentration preferably greater than 90°.

More especially still, the adjuvant integrated in the binary solvent and dissolved therein is constituted by an organic polymer selected in order not to limit the solubility of the active product in the main solvent.

More especially, the adjuvant is constituted by an organic polymer, soluble in lower alcohols and in water.

Finally, the adjuvant is more especially still selected from the family of polymers comprising:

the Monoglycerides
the Diglycerides
the Polyethylene Glycols (PEG)
Esters and Ethers of alcohol amines
Esters and Ethers of Diethanol amines
Esters and Ethers of isopropanolamines
Esters and Ethers of Monoethanolamines
Ethoxylamine
Ethoxylated derivatives of fatty acids
Polyether-alcohol of alkylamyl
Polyether-alcohol of alkanolamide
The Esters and Ethers and in particular:
Acid esters of mono and diglycerides
Esters of fatty acids
Esters of Polyethylene Glycol (PEG), particularly monolaurate, stearate, distearate of PEG.
Esters and Ethers of Propylene Glycol
Esters and Ethers of Polyglycerol
Esters and Ethers of Polyglycol
Esters and Ethers of Glycol
Ethoxylated derivatives of alcohols and fatty alcohols and Phenols
Propoxylated derivatives of fatty alcohols and alkylphenols
Ethoxyalkylphenol
Esters of Sorbitane particularly Monostearate of Sorbitane
Esters of Saccharose particularly Palmitate and Stearate of Saccharose
Polyoxyethers of Glycol, of Sorbitane, of Glycerol
Lecithins and derivatives
Alklyloamide
Ethoxylated, hydrogenated Castor oil
Esters of ethoxylated Sorbitane
Esters of ethylene glycol
Copolymers and polymers of Ethylene and propylene oxide
Derivatives of ethanolamide of fatty acids
Derivatives of diethanolamide of fatty acids
Polycondensates of ethylene oxide
Polycondensates of polypropylene glycol According to another characteristic, the adjuvant is introduced in the binary solvent system in a proportion of between 10% and 60% by total weight of the binary solvent.

According to yet another particular feature, the substrate will be selected from the family comprising edible carbohydrates.

And more especially still, the substrate is constituted by sorbitol or mannitol.

According to one embodiment of the method of the invention, the impregnation and absorption of the solution by the substrate is continued up to saturation and the obtaining of a homogeneous preparation of the solution adsorbed in the substrate, and this both within each granule and at the level of the granules between one another.

And according to a characteristic of implementation of the method, the substrate undergoes several successive cycles of enrichment in microcrystals, each cycle comprising an impregnation phase followed by an evaporation phase, the cycles being repeated until saturation of microcrystals is optimum.

The invention also relates to a medicinal specialty in galenical presentation and constituted in particular by a pastille, granule, pill, tablet or the like, adapted to be sucked by the user and for sublingual administration, characterized in that it comprises at least one active product in microdispersed form within a substrate, such microdispersion having been obtained in accordance with the method specified hereinabove.

And more particularly, the specialty comprises an active product microdispersed within a substrate and included in the spongy or cellular structure thereof in the form of microcrystals, the size of the microcrystals generally being less than 10 microns.

In accordance with an embodiment of the specialty according to the above characteristics, the active product is constituted by aspirin reconstituted in the form of microcrystals with a support constituted by sorbitol.

And more particularly, the medicinal specialty described above and based on microdispersed aspirin comprises an acidifying agent such as citric acid or equivalent acidifying agent.

The composition of each tablet is based on a percentage of aspirin in the form of microcrystals included between 10 and 200 milligrams on a substrate such as sorbitol whose weight is included between 100 and 2500 milligrams.

And according to a more particular embodiment, the medicinal specialty is characterized in that it comprises in synergetic combination, in addition to the aspirin in microdispersed form, one or more auxiliary active products selected from the families comprising:

antiseptics (such as quaternary ammoniums, chlorexhidine)

antibiotics (such as Bacitracine, Tyrothricine, Fusafungine)

local antifungal agents (such as miconazole, nystatine, amphotericine B)

anti-viral agents (such as Acyclovir, Azido-thymidine (AZT), interferons)

cicatrizing agents (allantoin, azulene)

enzymes (such as lysozyme, papain, bromeline)

analgesics (such as procain, tetracain, stovain).

Some embodiments of the invention have been described hereinafter, applied in particular to the manufacture of a therapeutical specialty based on aspirin, but said method is adapted in the same manner to a large number of therapeutical substances having comparable physico-chemical characteristics (weak solubility in water, aggresivity towards the tissues, bad taste, poor tolerance) or an imperfect bio-availability in the digestive tract or a short biological half-life of a few hours to a few minutes, this by way of indicative and non-limiting example, such as diltiazem, nifedipine, molsidomine, amiodarone, bepridil, prostacycline and its analogues, ticlopidine and its analogues, or all peptidic substances with anti-cancerous or hormonal action.

According to a first embodiment of the invention, the latter comprises the different phases described hereinafter.

Phase 1

A binary solvent is prepared, comprising, as main solvent, an alcoholic solvent constituted by a lower alcohol such as ethanol.

And in this base is incorporated and dissolved an adjuvant constituted by polyethylene glycol (PEG 6 000) introduced in a proportion included between 0.5 and 4 parts.

3 to 5 parts of aspirin are incorporated in the mixture thus constituted by 10 to 20 parts of ethyl alcohol (95° ethanol) and by 0.5 to 2 parts of PEG.

The optimum proportion lying between 6 and 8 parts of the binary solvent at a minimum for 1 part of aspirin.

Phase 2

This aspirin solution is preferably distributed over a support of sorbitol type or any other water-soluble substrate and usable in the formulation of tablets to be sucked via mixers conventionally used in pharmacy.

The sorbitol thus employed presents a cross-linked structure as visible in accompanying photo No. 1.

Under these conditions, the particles of the substrate formed from sorbitol are impregnated with the solution in totally homogeneous manner both within the same particle and at the level of the particles with respect to one another.

The impregnated particles of sorbitol are then dried in a vacuum evaporator at ambient temperature.

And the impregnation and evaporation cycle is continued repeatedly until optimum saturation is attained of the microcrystals of aspirin within the substrate of sorbitol.

Phase 3

The aspirin thus reconstituted in microdispersed form within the sorbitol substrate is, after sifting, mixed with any product, medicinal or not, intended to improve the therapeutical efficiency, the taste or presentation and also facilitating the technical methods of manufacture.

Phase 4

After homogenization, the mixture constituted by particles or granules of sorbitol internally containing the microcrystals of aspirin, themselves adhering to the walls of the sorbitol thanks to the presence of the PEG serving as binding agent, is then subjected to compression by the conventional apparatus in order to obtain the pastilles, tablets, granules or pills.

All along the different phases for carrying out the method, the presence of the PEG makes it possible to solve the problems of manufacture. Initially, the PEG does not modify the solubility of the active principle (Aspirin) but participates in limiting the crystalline reconstitution of the aspirin within the substrate, and therefore allows the better microcrystallized state. It also gives the substrate a morphology of regular spongy granule, as appears on photo No. 2.

Any problem associated with separation (lack of homogeneity) of the microcrystals of aspirin with respect to the substrate is also avoided; the residual PEG left in situ after evaporation of the main solvent then constitutes the binding agent which allows firm adhesion of the microcrystals on their adsorption wall.

Consequently, from the stage of evaporation, losses at manufacturing level are avoided.

The microcrystals being regularly distributed within the substrate of sorbitol, such homogeneous distribution remains and is consequently found again at the level of the finished products whose composition is thus maintained constant.

The PEG introduces, furthermore, a veritable coating of the particles of sorbitol and such coating allows, in addition, a very good plasticity of the mixture during the compression phase.

All along the life of the product, the homogeneity of the whole being ensured, one is certain of finding at administration level the quality and quantity of active product which was programmed.

Finally, by ensuring the successive cycles of enrichment of the substrate (each cycle comprising a phase of impregnation and a phase of evaporation), the dosage of the tablets may be adjusted exactly from 10 milligrams of acetylsalicylic acid per tablet weighing from 300 to 500 mg.

And this dosage is adequate to obtain a therapeutic effect by local route, particularly in contact with the lesions or by sublingual route at the level of general organic disorders such as for example certain cardiovascular diseases.

Thus, for other molecules, the quantity of active principle for local or general use may also be perfectly adjusted.

According to another characteristic, one proceeds, before the final phase of forming tablets and in the formulation of the latter, with the incorporation of an acidifying agent such as citric acid.

This agent, during administration, makes it possible slightly to acidify the salivary dissolution medium by establishing it between pH 3 and 4.5; this acid medium protects the aspirin from a hydrolyzing attack, increases its speed of dissolution in the saliva and facilitates its contact and passage through the mucous membranes.

According to another advantage of the invention, the PEG has also made a coating of the microcrystals which, whilst binding them firmly to the substrate of sorbitol, protects them from the phenomena of hydrolysis and of deacetylation, namely the transformation of Acetylsalicylic Acid (aspirin) into Salicyclic acid, this with production of acetic acid. The PEG therefore ensures not only a physical fixation of the microcrystals, but also the protection of their chemical quality.

According to another development of the invention, hydrocolloidal polymers are introduced in the formulation of the tablet, by incorporation in the sorbitol laden with microcystals of aspirin, in a proportion of between 0.5 and 5%.

The presence of these polymers, after obtaining all the microcrystals on supports, makes it possible to employ a substance of polymeric type whose role is to form a hydrophilic matrix or gellified network; the latter is thus continuously hydrated by the saliva on the periphery of the tablet and it is reconstituted as soon as it disintegrates upon contact with the saliva in the buccal cavity.

Too rapid a release of the crystals of aspirin which would come directly into contact with the mucous membrane and exert thereon their aggressive power due to their too slow dissolution, is thus avoided.

A considerably improved local tolerance of the product is thus allowed, since the aspirin is thus partially and previously dissolved before being released from the pharmaceutical form; thus allowing its rapid assimilation and avoiding its aggressive stagnation at the level of the mucous membrane.

Among the hydrocolloidal polymers which may be used, mention will be made of gum arabic, gum tragacanth, pectines (polygalacturonic acid), alginic acids and derivatives, carragheenins, agar-agar, guar gum and carob.

Cellulose derivatives such as: methylcellulose, hydroxyethylcellulose, hydroxypropylcellulose, carboxymethylcellulose, hydroxpropylmethylcellulose, methylethylcellulose.

Synthetic polymers such as polyvinylpyrrolidone, polymers of carbovinylic acid (carbopol).

Inorganic derivatives such as bentonite, montmorillonite, weegum (Registered Trademark).

Polymers of biological origin such as: xanthane, gelatin, scleroglucane, dextran.

Modified starches such as carboxymethyl starch, hydroxyethyl starch, hydroxypropyl starch and their salts.

Figure 1:
FIG. 1 is a microphotograph showing the state of the sorbitol base.
Figure 2:
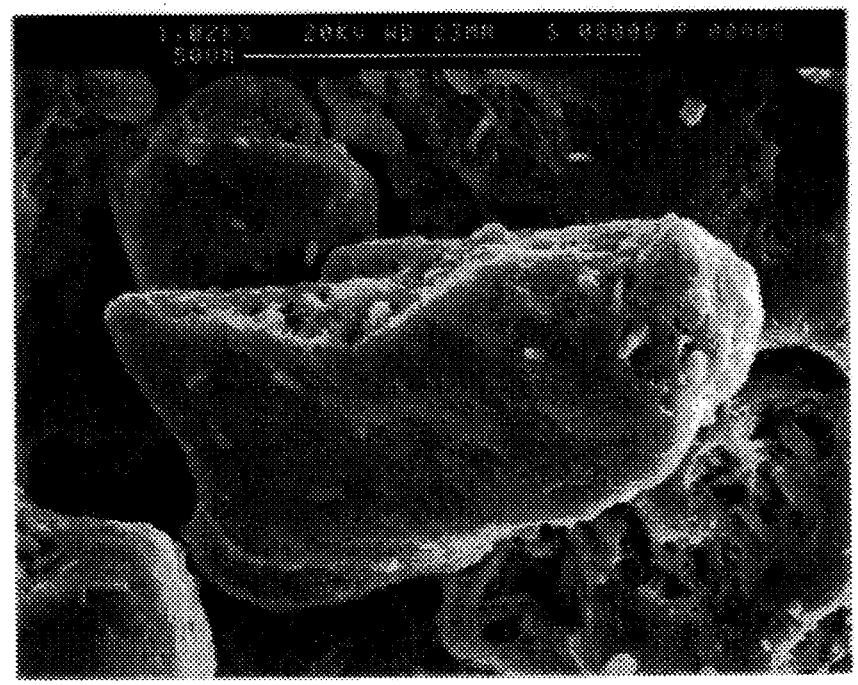
FIG. 2 is a microphotograph of granulates of sorbitol containing microdispersed aspirin and coated with PEG after application of the method.

A method of manufacture will be described hereinafter:

1—Unitary formula:

| COMPONENT | QUANTITY | FUNCTION |
| --- | --- | --- |
| Acetylsalicylic acid | 100 mg | Active principle |
| PEG 6000 | 125 mg | Binding agent - protector - volume regulator |
| Citric acid | 10 mg | pH corrector |
| Sorbitol W60 type | 950 mg | Support |
| Xanthane | 15 mg | Gelling agent |
| Aspartam | 7 mg | Sweetener |
| Orange aroma | 10 mg | Aromatizing agent |
| Na stearylfumarate | 20 mg | lubricant |
| 96% ethanol | V/V | Auxiliary of manufacture |

2—Manufacturing formula:

For a batch of 4000 multiple or sub-multiple tablets

| COMPONENT | QUANTITIES | SUPPLIERS |
| --- | --- | --- |
| Acetylsalicyclic acid | 400 g | Rhône-Poulenc |
| PEG 6000 | 500 g | |
| Pulverulent, anhydrous citric acid | 40 g | |
| Sorbitol W60 | 3800 g | Roquette |
| Xanthane | 60 g | Kelco/Sanofi - Bio industrie |
| Aspartam | 28 g | Searle-SPCI |
| Orange aroma | 40 g | Robertet |
| Na stearylfumarate | 116 g | |
| 96% V/V ethanol | 1600 g | |

3—Equipment

1—Scales weighing up to 4600 g, with a precision of 0.05 g, of METTLER PM type

2—Scales weighing up to 36 kg with a precision of 0.1 g, of the METTLER PK 36 type 3—Stainless steel vat with a capacity of 5 liters, provided with a double jacket and a heating/cooling system.

4—Pneumatic stirrer of REXXON type provided with a stirring blade.

5—Granulator-drier mixer, of the TOPO GRANULATEUR or TURBOSPHERE MORITZ type

6—Calibrator FREWITT equipped with a grid of 1.2 mm mesh opening

7—Rotary mixer of ROEHN wheel type equipped with a container with a capacity of 10 liters 8—Compressing press of FETTE P 1000 type, equipped with flat, bevelled stamps, 19 mm in diameter.

4—MODUS OPERANDI

Step 1

In a stainless steel, 5-liter vat, introduce:

1600 g of 96% V/V ethanol.

By circulating hot water in the double jacket, take the temperature of the alcohol to 30° C.±2° C.

Step 2

Introduce in the Ethanol:

500 g of PEG 6000

Stir the solution for 15 minutes until the PEG 6000 has completely dissolved.

When the PEG 6000 is entirely dissolved, cool the solution to +18° C.±2° C.

Step 3

Introduce, with stirring, 400 g of acetylsalicylic acid into the preceding solution.

Step 4

In the vat of the mixer-granulator, introduce:

3800 g of W 60 sorbitol with lumps previously removed

After closure of the apparatus, homogenize the mixture at speed III for 5 minutes.

Take the temperature of the double jacket of the apparatus to 50° C.

Maintain the speed of rotation on III during the whole manufacture.

Step 5

When the temperature of the sorbitol reaches 30° C, reduce the pressure of the vat to minus 700 mbar.

Introduce, by fractions of 100 ml, the alcoholic solution of acetylsalicylic acid.

Between each fraction introduced, operate the predrying cycle of 2 minutes in accordance with the following parameters:

breaking of the vacuum for 10 seconds and return to ambient pressure, re-establishment of the vacuum at minus 700 mbar for 30 seconds.

Rocking of the granulator with reversal of the direction of rotation of the mixer.

During the whole operation of impregnation/drying, the temperature of the sorbitol mixture must be included between 28 and 30 degrees Centigrade (Tolerance 25° to 35°).

Step 6

When the whole of the aspirin solution has been impregnated on the sorbitol, dry the preparation for 25 minutes in accordance with the cycle used in step 5.

At the end of drying, the temperature of the product must be included between 35° C. and 40° C.

Step 7

Reduce the speed of stirring to I and cool the preparation to ambient temperature.

Step 8

Calibrate the preceding dry mixture on a FREWITT calibrator equipped with a grid of 1.2 mm mesh opening.

Collect the calibrated grain in the vat of the ROEHN wheel mixer.

Step 9

Introduce into the vat of the ROEHN wheel mixer:

aspartam xanthane orange aroma

Na stearylfumarate

Homogenize the mixture by 15 minutes' stirring at the speed of 20 rotations per minute.

Step 10

In a room with controlled hygrometry whose relative humidity is close to 20%, compress the mixture prepared in the preceding step on the rotating press equipped with stamps of 19 mm diameter.

Adjust the parameters of the compression to obtain tablets with the following characteristics:
average weight: 1236 mg Tolerance: ±5%
Hardness: 8 kg Tolerance 6 to 12 kg After manufacture, the tablets are packed in accordance with the usual techniques adapted to this type of product.

The invention presents a very broad domain of application. In fact, a high number of pharmaceutical substances presents physical and/or chemical characteristics which do not predispose them to a good dissolution in the aqueous mediums of the organism.

In addition, certain of these substances are of such nature as to irritate the tissues of the digestive tube, they do not support the presence of food substances which modify their bio-availability and, to compensate these drawbacks, the obtaining of the therapeutic effect may necessitate a high dosage.

Often, such increases in doses themselves generate increased disorders as a function of the patient's personal sensitivity, from the digestive or general standpoint.

It is therefore interesting for major substances such as anti-inflammatories, which must treat stomatological and/or otorhinolaryngological affections, to place them directly and locally in contact with the lesions, whilst reducing their unpleasantness and their aggressivity for the tissues.

It is also interesting, whether it be for anti-inflammatories, as for other products with cardiovascular, or diuretic, or pulmonary vocation, or of the central nervous system, or anti-viral, or immunostimulant or anti-cancerous, or with hormonal action or having other therapeutic effects, to be able to administer them without unpleasantness by the sublingual route.

To that end, the aggressive character for the sensitive tissues of the mouth or unpleasant for the taste, of said substances must have been reduced but also the best possible dissolution in the saliva must have been prepared, in order that the greatest quantity of substance administered passes by this route in the shortest time.

This requires that the principles which preside manufacture of said compounds allow, on the one hand, this better and rapid dissolution which is expected, without unpleasantness and, on the other hand, that these manufacturing principles be compatible with the technical requirements and means usual in the pharmaceutical industry, the constraints of stability applied to the products by the regulations finally and especially compatible with the lowest possible industrial cost prices, as the requirements of low costs given to medicaments are well known.

We are thus presenting a method which, in its totality, solves firstly the problems of employing microadsorbed active principles to allow better dissolution thereof in the saliva and to reduce the unpleasantness of said substances; the same method also solves the technical manufacturing problems encountered with the microadsorbed substances, which have not yet been solved up to the present time; and, finally, said method does not increase the cost price of these innovating products thus constituted which contribute to the Medical Corps and to the public, new facilities and simplicities of treatments for numerous disorders.

The invention has been described more particularly in connection with a galenic presentation of aspirin.

In fact, this crystalline substance, sparingly soluble in water, precipitates and actively crystallizes as soon as it comes into contact with the very acid pH (pH 1.5) of the gastric mucous membrane.

This rapid crystallization is at the origin of intolerances found in the majority of subjects, and it has been demonstrated that gastric mucous membranes in contact with Aspirin all bleed, even the healthy ones.

Thus, if a bucco-dental or pharyngo-laryngeal inflammation is to be treated, it appears disproportionate to take aspirin by the general route (reaction at stomach level), whilst a quantity, ten times less, of Aspirin placed in contact with the lesion suffices to produce, locally, the desired anti-inflammatory/antalgic effect.

However, this is not applied, as Aspirin has an unpleasant taste and its acidity is difficult to tolerate.

Similarly, it is well known that small quantities of Aspirin (from 50 to 200 mg per day) may efficiently protect from the occurrence of thromboses of the coronary arteries by an anti-aggregating action.

The regular taking of Aspirin for this purpose of prevention over a long period proves, there again, impossible, due to the irritating effects and bleedings provoked at stomach level.

The method which is presented makes it possible to produce, on the one hand, tablets of Aspirin to be sucked, which treat locally, efficiently and pleasantly, bucco-pharyngo-laryngeal inflammations, on the other hand, to propose the regular taking of Aspirin tablets issuing from the same method at a dose of 20 to 150 mg by the sublingual route for the prevention of cardio-vascular risks, there again without any local unpleasantness or unpleasant taste. Other substances completing this specific action may also be added to the Aspirin.

Other substances still may usefully employ the method to improve their bio-availability and therapeutic efficiency: by way of example, nifedipine, sparingly soluble in water, presented in the form of capsules with enteral dissolution/release.

Now, this major anti-coronary may protect from the occurrence of a sudden infarctus from the first signs, on condition that it is rapidly admitted into the circulation. In this particular case, a tablet issuing from the method may be rapidly dissolved under the tongue and the active substance, nifedipine, passes in a few seconds into the circulatory flow to act immediately at the level of the heart.

We claim:

1. A method for preparing a therapeutical composition for internal use, in galenic presentation, and containing at least one active principle of slightly or non-hydrosoluble nature in solid form within a substrate of cross linked structure, especially an edible carbohydrate, the active product being distributed therein in the state of finely dispersed microcrystals, and the method comprising the steps of:

(a) preparing an organic solvent of the said active principle and an adjuvant constituted by a hydrocolloidal organic polymer having hydrophilic properties, said polymer being soluble in said solvent and in a solid state at ambient temperature;

(b) incorporating and dissolving said adjuvant in said solvent within a percentage ranging from 10 percent to 60 percent of the total weight of the solvent, at a temperature ranging from 30° C. at the beginning of the dissolution to 18° C. at the end of the dissolution;

(c) dissolving the said active principle in said solvent to obtain a solution of both adjuvant and active principle within said solvent, on the basis of substantially one part of active product for between 6 and 8 parts of the solution formed by the solvent and the adjuvant in solution therein;

(d) impregnating the thus obtained solution on a substrate of cross linked structure constituted by an edible carbohydrate until the solution is homogeneously absorbed within the substrate, said impregnation being conducted at a temperature of the edible carbohydrate ranging from 25° C. to 35° C. and under reduced pressure of substantially 700 mbar;

(e) evaporating by drying in vacuo at ambient temperature the solvent from the solution within the substrate in order to obtain simultaneous deposition of microcrystals of active principle and of the adjuvant in solid state, within the cross linked structure of the substrate, the solidification of the adjuvant forming a protective coating for said individual microcrystals, and thus limiting the crystalline spread and the size of the microcrystals, which size is limited to 10 µ or less, while binding and cementing them and thus avoiding their entrainment by eluation during evaporation;

(f) repeating a cycle including steps (d) and (e) until a predetermined proportion of the microcrystals of active principle with hydrocolloidal coating is absorbed and finely dispersed within the substrate; and (g) submitting the said substrate to compression in an ambiance of controlled hygrometry of substantially 20 percent to form tablets, granules or pills, within which each individual microcrystal is coated by hydrocolloidal polymer forming an hydrophilic matrix ensuring during compression and after administration, especially per os, physical and chemical protection of each individual microcrystal of said active agent, thus avoiding direct aggressive and stagnant contact of the microcrystals of active agent with the mucous membrane and an unpleasant taste, the said hydrocolloidal polymer furthermore ensuring regular dissolution of the microcrystals within the hydrophilic matrix impregnated by biologic liquid such as saliva and subsequent absorption in soluted state within the body.

2. Method according to claim 1 wherein the hydrocolloidal organic polymer is a polyethylene glycol.

3. Method according to claim 1 wherein the solvent is a monofunctional alcohol with low vapor tension selected from the group consisting of the methanol, ethanol, butanol and propanol.

4. Method according to claim 1 wherein the active principle is selected from the group comprising aspirin, diltiazem, nifedipine, molsidomine, amiodarone, bepridil and prostacycline, each offering weak solubility in water, aggressivity towards the tissues, bad taste, and poor tolerance.

5. Method according to claim 1 wherein the hydrocolloidal polymer is introduced in the solvent in a proportion from 10 to 60 percent of the total weight of the solvent.

6. Medicinal speciality in galenic presentation and constituted in particular by a pastille, granule, pill, tablet or the like, adapted to be sucked by the user or with sublingual administration, having been obtained in accordance with the method according to claim 1 wherein it comprises:

(a) an edible substrate of porous and cross-linked structure;

(b) a hydrophilic matrix constituted by a hydrocolloidal polymer forming a gellified network absorbed inside of the cross-linked structure of the said substrate;

(c) an active product sparingly soluble in water in the form of microcrystals, the size of which is of the order of 10 µ or less, dispersed inside of the said hydrocolloidal polymer, said active product thus being prevented from direct contact with the mucous membrane and being subject to dissolution within the hydrocolloidal polymer impregnated by biologic liquid after administration to the body.

7. Medicinal specialty according to claim 6 wherein the hydrocolloidal organic polymer is a polyethylene glycol.

8. Medicinal speciality according to claim 6 wherein the substrate is an edible carbohydrate.

9. Medicinal specialty according to claim 6 wherein the active principle is selected from the group comprising aspirin, diltiazem, nifedipine, molsidomine, amiodarone, bepridil and prostacycline, each offering weak solubility in water, aggressivity towards the tissues, bad taste, and poor tolerance.

10. Medicinal specialty according to claim 6 wherein the active product is incorporated within the substrate on the basis of a weight percentage of from 10 to 200 mg of active product for from 100 to 2500 mg of substrate, the active product being dispersed within a hydrocolloidal organic polymer on the basis of a weight percentage of 1 part of active product for from 6 to 8 parts of hydrocolloidal polymer.

* * * * *